United States Patent [19]

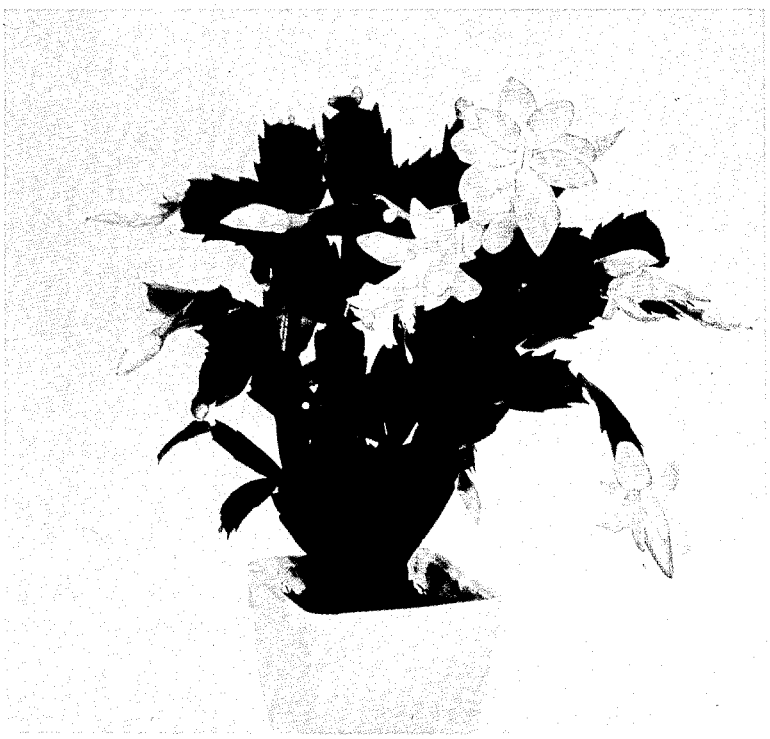
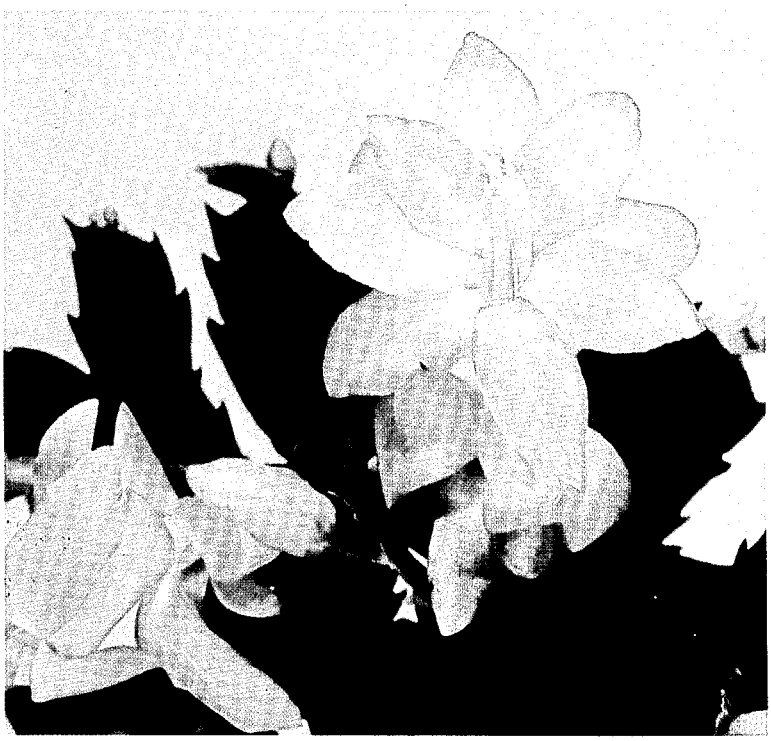

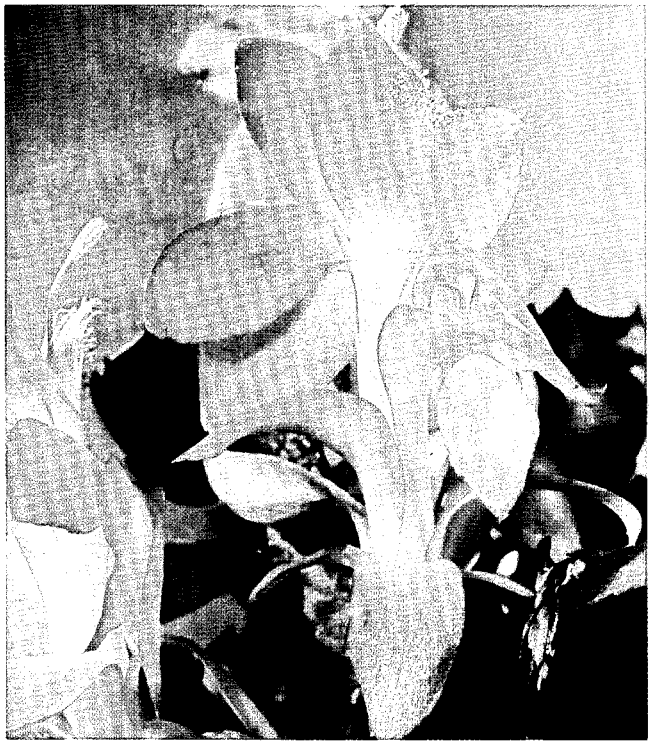
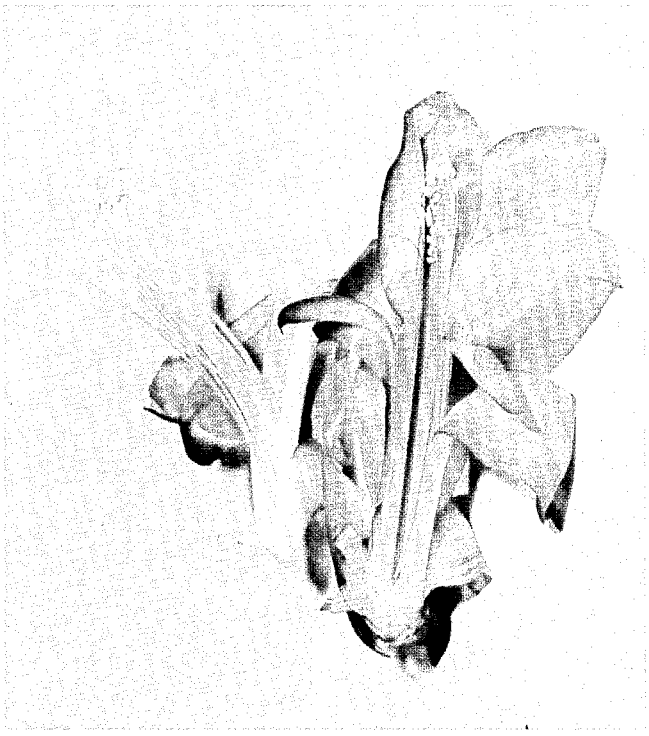

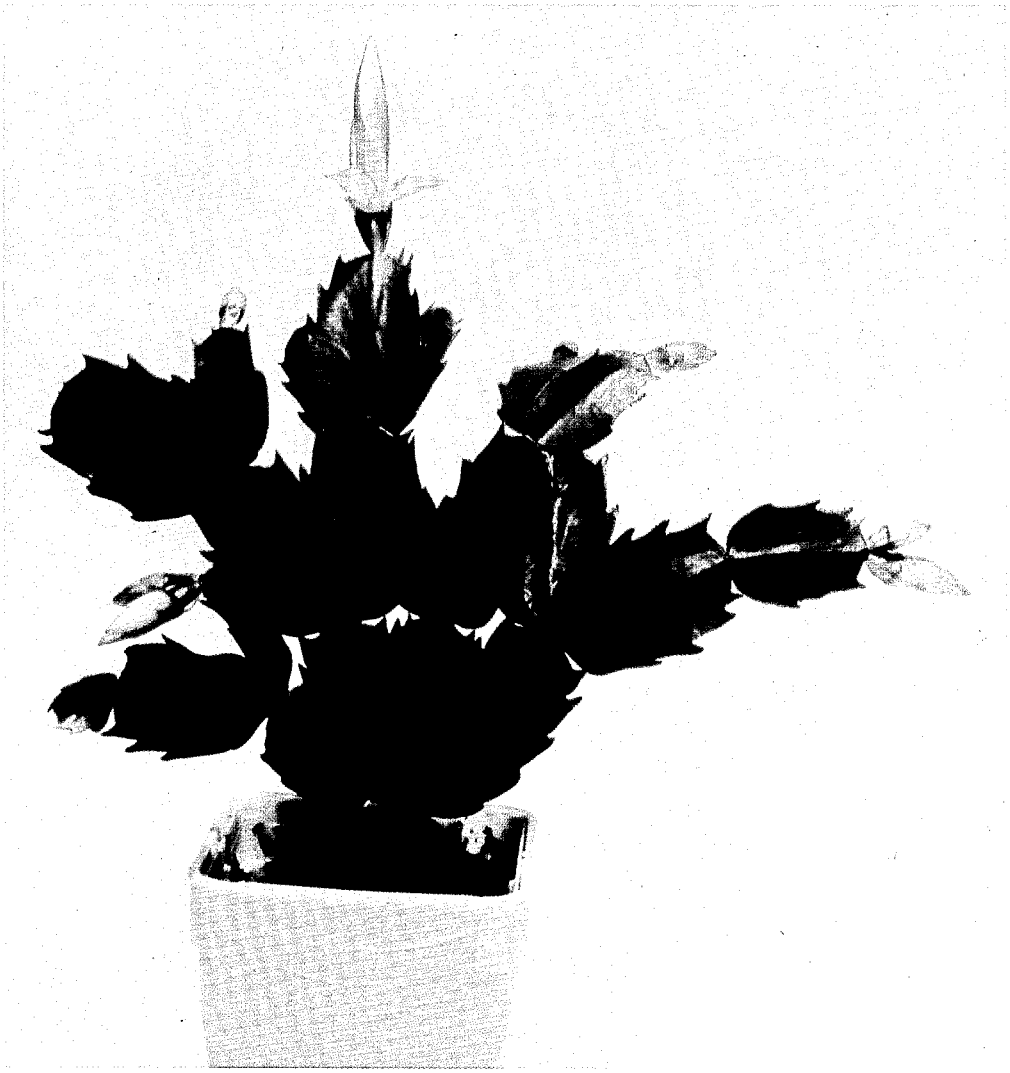

Cobia et al.

[11] Plant 4,198

[45] Jan. 24, 1978

[54] CACTACEAE PLANT

[75] Inventors: Barnell L. Cobia, Winter Garden; Stephen H. Griffith, Apopka, both of Fla.

[73] Assignee: B. L. Cobia, Inc., Winter Garden, Fla.

[21] Appl. No.: 760,419

[22] Filed: Jan. 18, 1977

[51] Int. Cl.[2] ..... A01H 5/00

[52] U.S. Cl. ..... Plt./88

[58] Field of Search ..... Plt./88

*Primary Examiner*—Robert E. Bagwill

*Attorney, Agent, or Firm*—Roger L. Martin

[57] ABSTRACT

A new and distinct variety of the Cactaceae family is related to the *Zygocactus truncatus* 'Kris Kringle' and *Zygocactus truncatus* 'Lavender Doll' varieties provides specimens with a natural tendency to branch during the growth period preceding blooming without the need for inducement by pruning. The specimens have a fast growth rate which provides an upright, compact appearance and wherein the phylloclades have generally shorter midribs than those of the 'Lavender Doll' variety and generally thicker teeth than those of the 'Kris Kringle' variety. The specimens exhibit resistances to nutrient deficiencies, fungus type diseases and flower bud abscission that are comparable to those of the 'Kris Kringle' and 'Lavender Doll' variety and the flower appears later than that of the 'Kris Kringle' variety and has a bloom life of from about 6 to about 9 days. The flower hues are red, pink, purplish red and/or yellowish pink.

1 Drawing Figure

The invention relates to a new and distinct plant variety of the Cactaceae family and which has been named the *Zygocactus truncatus* 'Red Radiance' by the inventor.

Certain plant varieties of the Cactaceae family are well known in the foliage plant market and among those are those of the *truncatus* species of the Zygocactus genus. These varieties tend to bloom in the months of November and December in the Northern Hemisphere and hence they appear in the retail market area primarily during the Thanksgiving and Christmas seasons and wherein they are commonly referred to as a "Christmas Cactus".

The *Zygocactus truncatus* 'Kris Kringle' forms the subject matter of U.S. Plant Pat. No. 3,688 and has a heritage that includes the variety known commercially as 'Christmas Cheer' and the variety known as *Zygocactus truncatus* 'Parma'. It has a "reddish" colored bloom and a bloom life which provides a suitable shelf life at the retail level of sales. The variety also has a fast growth rate with substantial resistances to nutrient deficiencies and to fungus type diseases. The 'Kris Kringle' variety also has a substantial resistance to flower bud abscission and is endowed with a natural tendency to branch without inducement by pruning during the growth period preceding blooming. The growth rate, resistances, and branching tendencies are much sought after by growers of the so-called "Christmas Cactus" varieties.

The *Zygocactus truncatus* 'Lavender Doll' is yet another recent development among the so-called "Christmas Cactus" varieties and it forms the subject matter of a U.S. Plant Pat. No. 3,690. The 'Lavender Doll' variety has a heritage that also includes the 'Christmas Cheer' variety and it has a growth habit which includes the mentioned resistance characteristics attributed to the 'Kris Kringle' variety but the natural tendency to branch without inducement by pruning during the growth period preceding blooming is not as profuse as that resident in the 'Kris Kringle' variety. The 'Lavender Doll' has what may be called a "purplish" colored bloom and like the 'Kris Kringle' variety, has rapidly acquired a broad market acceptance that has created a demand among nurserymen for different colored varieties of the so-called "Christmas Cactus" types and which have the growth rate and natural resistances to nutrient deficiencies, fungus type diseases and flower bud abscission that are exhibited by the 'Kris Kringle' and 'Lavender Doll' varieties.

The general objective of the invention has been to develop a variety of the *truncatus* species which has the growth rate and previously mentioned resistance characteristics that are associated with the 'Kris Kringle' and 'Lavender Doll' varieties but which has color characteristics that are distinguishable from those of such varieties and a bloom that matures later than that of the 'Kris Kringle' variety.

The objectives of the invention have been fully realized by the development of the new plant variety described hereinafter in detail. The new plant variety was developed in a nursery located at Winter Garden, Fla., as a hybrid secured by cross-pollinating the flower of a plant specimen of a variety developed by the inventor from a vegetative mutation that appeared on a specimen of the 'Lavender Doll' variety with pollen from a plant specimen of the 'Kris Kringle' variety. The maternal variety is a research variety which has not appeared in the marketplace and it is distinguishable from the 'Lavender Doll' variety primarily by a growth habit which produces slightly larger phylloclades and specimens with somewhat poorer natural branching tendencies than those exhibited by the 'Lavender Doll' variety. The seeds taken from the fertilized seed pod of the maternal variety were cultivated at the mentioned nursery location, and after prolonged observation of the seedlings, the hybridized plant of the new plant variety was selected and asexually reproduced by the inventors at the Winter Garden nursery through a propagation of stem cuttings taken from the original hybrid plant.

Through successive propagations, it has been ascertained that specimens of the new plant variety generally resemble the parent varieties but are distinguishable from the parent varieties and from other related varieties known to the inventors by a growth habit which is evident in specimens propagated and grown under nursery conditions utilized in the growing of tropical plants at Winter Garden, Fla. as combining the following principal characteristics:

1. Specimens with an upright compact appearance having phylloclades with generally shorter midribs than those of the 'Lavender Doll' variety and with generally thicker teeth than those of the 'Kris Kringle' variety.

2. A natural tendency to branch without inducement by pruning during the growth period preceding blooming and which is comparable to that of the 'Kris Kringle' variety.

3. A fast growth rate with resistances to nutrient deficiencies, to fungus type diseases, and to flower bud abscission that are comparable to those of the 'Kris Kringle' and 'Lavender Doll' varieties.

4. A flower which blooms from about one to three weeks later than the 'Kris Kringle' variety and has a bloom life of from about 6 to about 9 days and which has a. a sepaloid series of free tepals with marginal blade areas in the inner and outer whorl members that in color are dominated by reddish purple, purplish red and/or purplish pink hues and with center fields in the inner whorl members that in color are dominated by pink and/or yellowish pink hues in the basal areas of the fields and by pink, red and/or reddish orange hues in the distal areas of the fields.

b. a perianth tube laminating series of tepals with center fields which extend into the apex areas of the tepal blades and which in color are dominated by red, pink, purplish red and/or yellowish pink hues and with lateral marginal areas which in color are dominated by reddish purple, purplish red and/or red hues, c. A perianth tube forming series of basally united tepals that provide a perianth tube with a basic color which is dominated by yellowish pink and/or pink hues and on which is superimposed elongated, circumferentially spaced, stripes that are proximally extending colors found in the blade marginal areas and blades with marginal areas which in color are dominated by reddish purple and/or purplish red hues that merge inwardly with a center field that in color is dominated by pink and/or purplish pink hues, and d. a style which in color at its proximal end is dominated by a purplish pink hue and at its distal end is dominated by a purplish red hue.

The accompanying drawings serve, by color photographic means, to illustrate the new plant variety and wherein:

One sheet is a color photograph of an 11 month old plant specimen of the new plant variety with maturing buds, a second sheet contains photographs illustrating the bloom, and a third sheet embodies color photographs which further illustrate the bloom and parts thereof.

The following is a detailed description of the new plant variety with colors and hues, unless otherwise clearly indicated by the text through the absence of color notations, being named in accord with the ISCC-NBS method of designating colors (U.S. Department of Commerce, National Bureau of Standards, Circular 553, issued Nov. 1, 1955), the named colors being interpreted from color notations derived by comparison with the color specimens in the current "Neighboring Hues Edition" of the Munsell Book of Color, published by the Munsell Color Company, Inc., of Baltimore, Md. The following description is further based on observations of well fertilized plants of less than one year of age from initial propagation and which were grown under 50–75% shaded glasshouse nursery conditions in the Winter Garden, Fla., area and wherein temperatures range from 60° to 85° F. during the winter months, from 75° to 95° F. during the summer months and are ambient during intervening periods.

DETAILED PLANT DESCRIPTION

Name: *Zygocactus truncatus* 'Red Radiance'.

Parentage:

*Maternal.*—A research variety unavailable in the marketplace developed from a vegetative mutation that appeared on a plant specimen of the variety named *Zygocactus truncatus* 'Lavender Doll'.

*Paternal.*—*Zygocactus truncatus* 'Kris Kringle'.

Classification:

*Botanic* (*Britton and Rose, The Cactaceae, Constable and Co., Ltd., London* 1937, *Vol. IV*).—

| | |
|---|---|
| (1) Family: | *Cactaceae* |
| (2) Tribe: | *Cereeae* |
| (3) Sub-tribe: | *Epiphyllanae* |
| (4) Genus: | *Zygocactus* |
| (5) Species: | *truncatus* (Haworth) Schumann |

*Commercial.*—Thanksgiving-Christmas blooming cactus.

Form: Terrestrial, shade-loving, succulent, leafless plant with jointed and branched stems.

Stems:

*General.*—Irregular with usually mono-chotomous to polychotomous branching of both upright and pendulous, adventitiously rootable, flattened phylloclades that have a prominent midrib and prominently toothed lateral wings.

*Phylloclades.*—General: Elongated and flat with transversely elongated, areole bearing, truncated apex, with inwardly tapering basal wing margins that merge through a broad usually pointed basal juncture with the phylloclade therebelow, and with an axillary areole associated with each tooth. Midrib: General — Extends longitudinally of phylloclade and continuously through joints with laterally tapering cortex at wing insertions. Pith surrounding vascular bundles that branch and provide lateral extensions of the vascular system to marginal teeth. Texture — Smooth waxy epidermis with wax in small embedded scales and becoming corky in basal stem areas with age. Size (2–6 mos.) — Length: Usually between 36 and 55 mm. with the average for respective plant specimens being usually between 41 and 49 mm. Thickness: Usually between 2.3 and 7.6 mm. with the average for respective plant specimens being usually between 3.5 and 4.5 mm. Color (at maturity) — Commonly moderate yellow green (7.5 GY 5/6) (near 7.5 GY 5/4) (5 GY 5/6) (near 5 GY 5/4) and/or moderate olive green (7.5 GY 4/6) (7.5 GY 4/4). Wings: General shape — Generally flattened from midrib cortex to tooth insertions with slight thinning taper toward margins. Margins — Toothed (modified leaves). Texture — Succulent to leathery with smooth waxy epidermis having wax arranged in small embedded scales and becoming corky in basal plant areas with age. Size (2–6 mos. old) — Center thickness: Usually between 0.6 and 2.7 mm. Width (as measured from phylloclade axis to most offset lateral areole): Usually between 7 and 19.5 mm. Color (at maturity) — Commonly moderate yellow green (7.5 GY 5/6) (near 7.5 GY 5/4) (5 GY 5/6) (5 GY 5/4) and/or moderate olive green (near 7.5 GY 4/6). Teeth: General shape — Generally flattened and tapered along margins from wing insertions to an apex having a hyaline, single cell, pointed spine with nonpredictable bending. Adaxial marginal shape: Generally straight to slightly convex. Abaxial marginal shape: Generally straight with usually a slight median indentation which serves as a distal terminus for a straight to slightly convex proximal margin and as a proximal terminus for a straight to convex distal margin. Orientation — Usually projects generally distally of phylloclade base in an alternate arrangement. Margins — Entire. Texture — Succulent to leathery with smooth waxy epidermis having wax in small embedded scales and becoming corky in basal plant areas with age. Number — Usually 6 to 8 per phylloclade. Size (2–6 mos. old) — Center thickness: Usually between 0.5 and 1.7 mm. Areole to apex dimension (adaxial marginal side): Usually between 2 and 8 mm. for teeth located distally of basal teeth. Color (at maturity) — Commonly moderate yellow green (7.5 GY 5/6) (7.5 GY 5/4) (5 GY 5/6) (5 GY 5/4) and/or moderate olive green (7.5 GY 4/6). Areoles: Terminal areole — Large elongated oval-shaped with several acicular bristles, copious multicellular hairs, and several buds that may mature into either new phylloclades or flowers. The opposite ends of the terminal areole are located adjacent to subsidiary areoles which are in turn located at the axils of teeth that are located at the distal end of phylloclade. Axillary areoles — Acicular bristles without glochidia but having short, brownish to colorless, multicellular hairs. In areoles that are located below the teeth at the distal end of the phylloclade, there is usually only one bud that is frequently latent.

Buds: Unarmored, ovoid and chlorophyllous.

Flowers:

*General.*—Sessile, zygomorphic, usually solitary, terminal, perfect and epigynous with double hypanthium and tepals (undifferentiated whorled sepals and petals) having a spiral emergence as a perianth provided with a sepaloid series of free tepals, a tube laminating series of tepals, and a tube forming series of united tepals.

*Sepaloid series.*—General: Free tepals inserted on top of ovary. Shape: Deltoid in outer members of the whorl and grading inwardly in the whorl with tepals varying generally from lanceolate to elliptic. All tips are acute and margins are entire with sparse irregular teeth appearing mainly in apex areas of the inner members of the whorl. Texture: Succulent and glabrous outer whorl members and grading inwardly in the whorl to silken blades with fleshy basal areas. Number: Usually from 8 to 10. Size (at full bloom): Base-tip dimension — Usually less than 35 mm. Maximum width dimension — Usually less than 15 mm. Color: Outer Whorl members — Marginal blade areas that in color are dominated by reddish purple, purplish red and/or purplish pink hues and basal blade areas that in color constitute extension of the ovary color into the outer whorl member. Commonly grayish yellow (near 5 Y 7/4), pale greenish yellow (near 7.5 Y 8/4) (near 10 Y 8/4), grayish greenish yellow (near 7.5 Y 8/4) (7.5 Y 7/4) (near 10 Y 8/4) (10 Y 7/4), light greenish yellow (near 10 Y 8/6), moderate greenish yellow (7.5 Y 7/6) (near 10 Y 8/6) (10 Y 7/6), deep greenish yellow (near 10 Y 6/8), dark greenish yellow (near 10 Y 6/8) (10 Y 6/6), light yellow green (near 2.5 GY 8/6), moderate yellow green (2.5 GY 7/6) (2.5 GY 6/6) (near 2.5 GY 6/4) (2.5 GY 5/6) (near 5 GY 5/6) and/or strong yellow green (2.5 GY 7/8) (2.5 GY 6/8) in basal blade areas. Commonly strong reddish purple (2.5 RP 5/10) (2.5 RP 4/10), moderate purplish red (5 RP 5/10) (5 RP 5/8) (5 RP 4/8) (7.5 RP 5/10) (near 7.5 RP 5/8) (7.5 RP 4/8) (10 RP 5/10) (near 10 RP 5/8), deep purplish pink (7.5 RP 6/10) and/or dark purplish pink (near 7.5 RP 6/8) in the marginal blade areas. Inner whorl members — Marginal blade areas that in color are dominated by reddish purple, purplish red and/or purplish pink hues which surround a center field that in color is dominated by pink and/or yellowish pink hues in the basal areas of the center field and by pink, red and/or reddish orange hues in the distal areas of the center field. Commonly strong reddish purple (2.5 RP 5/10) (2.5 RP 4/10), moderate purplish red (5 RP 5/10) (5 RP 5/8) (5 RP 4/8) (7.5 RP 5/10) (near 7.5 RP 5/8) (7.5 RP 4/8) (10 RP 5/10) (near 10 RP 5/8), deep purplish pink (7.5 RP 6/10) and/or dark purplish pink (near 7.5 RP 6/8) in the marginal blade areas. Commonly pinkish white (5 R 9/1) (10 R 9/1), pale pink (near 5 R 9/2), light pink (near 5 R 8/4), moderate pink (near 5 R 8/4), pale yellowish pink (10 R 9/2), light yellowish pink (near 7.5 R 8/4) (near 10 R 8/4) (near 2.5 YR 8/4) (near 5 YR 8/4) and/or moderate yellowish pink (near 7.5 R 8/4) (near 10 R 8/4) (near 2.5 YR 8/4) (near 5 YR 8/4) in the basal blade areas of the center field. Commonly deep pink (2.5 R 6/8) (near 5 R 6/10) (near 5 R 6/8), dark pink (5 R 6/6), grayish red (2.5 R 4/6), moderate red (near 2.5 R 5/10) (2.5 R 4/8) (5 R 5/10) (near 5 R 5/8) and/or moderate reddish orange (7.5 R 6/8) (7.5 R 5/10) (near 7.5 R 5/8) (10 R 6/8) (near 10 R 5/8) in the distal areas of the center field. Orientation at full bloom: Usually acute to recurved.

*Tube laminating series.*—General: Tepals inserted on ovary and basally united below the throat as outer laminations on the perianth tube and with progressively greater amounts of basal fusion inwardly in the whorl. Shape: Grading inwardly in the whorl with outer members having blades which are narrowly elliptic, lanceolate, and/or oblanceolate and inner members which are elliptic to lanceolate. All tips are acute and all margins entire with sparse irregular teeth mainly in the apex areas. Texture: Succulent, slightly fleshy basal areas with silken blades. Number: Usually from 4 to 6. Size (at full bloom): Base-tip dimensions — Usually between 35 and 59 mm. Maximum width dimensions — Usually between 11 and 16 mm. Color: A center field in the blade which extends into the apex area of the tepal, which in color is dominated by purplish red, red, pink, yellowish pink and/or reddish orange hues which merges with lateral marginal blade areas that are located proximally of the apex area and in color are dominated by reddish purple, purplish red and/or red hues, and which merges with a basal area that in color is usually translucent white, pinkish white, pale pink and/or pale yellowish pink. Basal blade areas are usually translucent white, pinkish white (5 R 9/1) (10 R 9/1), pale pink (5 R 9/2) and/or pale yellowish pink (near 10 R 9/2). Commonly moderate purplish red (7.5 R 5/8) (10 RP 5/10) (10 RP 5/8), moderate red (2.5 R 5/8) (5 R 5/10) (5 R 5/8), deep pink (near 2.5 R 6/8) (5 R 6/10) (near 5 R 6/8), dark pink (near 5 R 6/6), dark yellowish pink (7.5 R 6/6) and/or moderate reddish orange (7.5 R 6/8) (7.5 R 5/10) (7.5 R 5/8) (near 10 R 6/8) in the center field. Commonly strong reddish purple (10 P 5/10) (10 P 4/10) (2.5 RP 4/10), moderate reddish purple (near 10 P 5/8) (2.5 RP 5/8), moderate purplish red (5 RP 5/10) (near 5 RP 5/8) (5 RP 4/10) (5 RP 4/8) (7.5 RP 4/8) (10 RP 4/10) (near 10 RP 4/8) and/or moderate red (2.5 R 4/10) (2.5 R 4/8) (5 R 4/10) in the lateral marginal areas. Orientation at full bloom: Acute to recurved.

*Tube forming series.*—General: Tepals basally united to form hollow perianth tube that is inserted on ovary and equipped with irregular carina (keel) at throat. Shape: Perianth tube — Elongated and terete. Blades — Irregular and commonly lanceolate, oblanceolate and/or elliptic with acute tips and with tendencies for blade apex to be irregularly lacerate. Carina (keel) — Transcending, thin and irregular. Texture: Perianth tube — Thick, succulent and slightly ribbed. Blades — Translucent and silken. Carina (keel) — Fleshy. Blade number: Usually 8. Size (at full bloom): Perianth tube — Base to keel length: Usually between 31 and 38 mm. along axis of tube with average length difference between measurements along dorsal and ventral sides of respective specimens usually being between 0.5 and 6 mm. Internal major axis (at throat): Usually between 7 and 11 mm. When measured perpendicular to axis of perianth tube. Internal minor axis (at throat): Usually between 5 and 9 mm. When measured perpendicular to axis of perianth tube. Blades — Length (keel to tip): Usually between 23 and 37 mm. Width (maximum): Usually between 10 and 17 mm. Color (at full bloom): Perianth tube — Basic color is dominated by yellowish pink and/or pink hues and provided with elongated circumferential spaced stripes or striations that are superimposed on the basic color and proximally extending colors found in blade marginal areas. Basic color is usually pale yellowish pink (near 5 YR 9/2) (10 R 9/2) and/or pale pink (near 5 R 9/2). Blades — Marginal blade areas which in color are dominated by reddish purple and/or purplish red hues that merge inwardly with a center field that in color is dominated by purplish pink and/or pink hues. Commonly strong reddish purple (near 2.5 RP 5/10) (2.5 RP 4/10), moderate purplish red (5 RP 5/10) (near 5 RP 4/8) (7.5 RP 4/8) (10 RP 4/10) and/or dark purplish red (5 RP 3/8) in the marginal areas. Commonly pale purplish pink (5 RP 9/4) (near 5 RP 8/4) (7.5 RP 8/4) (near 7.5 RP 8/2), light pink (near 10 RP 8/4) (near 2.5 R 8/4) (near 5 R 8/4), moderate pink (near 10 RP 8/4) (near 2.5 R 8/4) (near 5 R 8/4), pale pink (5 R 9/2) and/or pinkish white (5 R 9/1) in the center field. Carina (keel) — Dominated by reddish purple and/or purplish red hues. Commonly strong reddish purple (10 P 5/10) (2.5 RP 5/10) (10 P 4/10) (10 P 4/8), moderate reddish purple (2.5 RP 5/8) (2.5 RP 5/6) and/or moderate purplish red (5 RP 5/10) (near 5 RP 4/8) (7.5 RP 4/8). Orientation at full bloom: Erect to recurved.

*Androecium (stamens).*—General: Numerous exserted and diadelphous stamens with one group having filaments basally fused to the perianth tube and the other group having filaments basally united to form a nectary housing, thin annulus around the style and which is provided with a thin, deflexed, irregularly toothed margin or ruffle at the throat of the annulus. Stamen number: Tube attached group — Usually between 80 and 86. Basally united group — Usually about 20. Filament: General — Translucent and glabrous with anther connective. Shape — Long and terete. Texture — Glabrous and silken. Color — A translucent white proximal end area that merges distally with a proximal area which in color is dominated by a purplish pink hue. Commonly moderate purplish pink (10 P 7/8) (10 P 7/6) (2.5 RP 7/6) and/or pale purplish pink (near 10 P 8/4) (2.5 RP 8/4). Size (at full bloom) — Length: Tube attached group — Usually between 34 and 51 mm. Basally united group — Usually between 40 and 48 mm. Diameter: Usually between 0.2 and 0.35 mm. intermediate the opposite ends. Anthers: General — Adnate with four longitudinally dehiscent pollen sacs. Shape — Elongated. Texture — Waxy. Color (before dehiscing) — Usually pale yellow (5 Y 9/4) and/or pale yellowish green (7.5 Y 9/4).

*Gynoecium (pistil).* —General: Compound, parietal placentation with united style surrounded by annular diffuse nectary at its insertion. Style: General — Stout and inserted in ovary. Shape — Elongated and terete. Texture — Fleshy and glabrous with short inner flutinous hairs at distal end. Color — Basal area has color dominated by purplish pink hue that merges with a distal end color that is dominated by a purplish red hue. Commonly pale purplish pink (near 2.5 RP 8/4) and/or moderate purplish pink (2.5 RP 7/6) (5 RP 7/6) (7.5 RP 7/6) in basal area. Commonly moderate purplish red (5 RP 4/8) (7/5 RP 4/8) (10 RP 4/8) at distal end. Size (at full bloom) — Length: Usually between 57 and 65 mm. Diameter: Usually between 0.7 and 0.9 mm. intermediate the opposite ends. Stigma: General — Exserted and erect with usually 7 or 8 inner marginally adhering lobes. Shape — Elongated and tapering toward lobe tips and having relatively blunt apices. Texture — Fleshy and smooth with short glutinous hairs. Color — Commonly light reddish purple (10 P 6/8) (10 P 6/6), moderate reddish purple (near 10 P 5/8) (2.5 RP 5/8) (2.5 RP 5/6) and/or strong reddish purple (10 P 5/10) (2.5 RP 5/10) (2.5 RP 4/10). Size (lobe length at full bloom) — Usually between 4.8 and 6.1 mm. Ovary: General — Epigynous with thin epidermis and distally located concavity and with single cavity having from 6 to 8 carpels with numerous ovules. Shape — Terete and ribbed and generally broadening from insertion to floral end. Texture — Succulent and glabrous with thin outer epidermis. Color — Commonly grayish yellow (near 5 Y 7/4), pale greenish yellow (near 7.5 Y 8/4) (near 10 Y 8/4), grayish greenish yellow (near 7.5 Y 8/4) (7.5 Y 7/4) (near 10 Y 8/4) (10 Y 7/4), light greenish yellow (near 10 Y 8/6), moderate greenish yellow (7.5 Y 7/6) (near 10 Y 8/6) (near 10 Y 7/6), dark greenish yellow (near 10 Y 6/8) (10 Y 6/6), deep greenish yellow (near 10 Y 6/8), light yellow green (near 2.5 GY 8/6), moderate yellow green (2.5 GY 7/6) (2.5 GY 6/6) (near 2.5 GY 6/4) (2.5 GY 5/6) (near 5 GY 5/6) and/or strong yellow green (2.5 GY 7/8) (2.5 GY 6/8). Size (at full bloom) — Length (insertion to concavity base): Usually between 9 and 13 mm. Major axis (distal end of concavity): Usually between 7 and 9 mm. Minor axis (distal end of concavity): Usually between 6 and 8.5 mm.

Growing characteristics: A fast growth rate with an upright and compact (dense) appearance as evidenced by erect stems with heavy (frequent) branching and a bloom life (from initial tepal separation to initial tepal withering) of from about 6 to about 9 days. A natural tendency to branch without inducement by pruning during the growth period before blooming and a resistance to bud abscission and nutrient deficiencies and to fungus type diseases that are comparable to those of the 'Kris Kringle' and 'Lavender Doll' varieties.

The following is a general description of a specimen of the new plant variety that was grown from the propagation of a single phylloclade in a nursery at Winter Garden, Fla.

Age of plant: 6 months from initial propagation.
Branches from propagated cutting: 2.
Total number of phylloclades grown from cutting: 21.
General:

| Branch No. | No. of Phylloclades | Max. Length mm. | No. of Tips |
|---|---|---|---|
| 1 | 9 | 190 | 4 |
| 2 | 12 | 192 | 6 |

Midribs:

| Branch No. | Length (avg.) mm. | Thickness (avg.) mm |
|---|---|---|
| 1 | 47 | 3.8 |
| 2 | 47 | 3.9 |

Wings:

| Branch No. | Center Thickness (avg.) mm. | Max. Width (Avg.) mm. |
|---|---|---|
| 1 | 1.5 | 11 |
| 2 | 1.3 | 13 |

Teeth:

| Branch No. | No./Phylloclades (avg.) | Center Thickness (avg.) mm. | Areole to Apex Dimension (avg.) mm. |
|---|---|---|---|
| 1 | 7 | 0.67 | 3.1 |
| 2 | 6 | 0.91 | 3.6 |

Phylloclade color: Moderate yellow green (7.5 GY 5/6) (5 GY 5/6) (near 5 GY 5/4).

The following is a general description of a flower of the new plant variety which was bloomed in December on a plant grown under shaded glasshouse nursery conditions in Winter Garden, Fla.

Bloom life: 8 days.
Sepaloid series of tepals:
*Number.* —9.
*Size (at full bloom).*—Maximum base-tip dimension: 31 mm. Minimum base-tip dimension: 3 mm. Maximum width dimension: 12 mm.
*Color.*—Grayish greenish yellow (7.5 Y 7/4) (10 Y 7/4) in major portion of the outer whorl members with margins which are moderate purplish red (5 RP 5/10) (7.5 RP 5/10). Inner whorl members strong reddish purple (2.5 RP 5/10) (2.5 RP 4/10) in the margin areas with median and basal colors which are light yellowish pink (near 7.5 R 8/4) (near 10 R 8/4) and/or moderate yellowish pink (near 10 R 8/4).
Tube laminating series:
*Number.*—6.
*Size (at full bloom).*—Maximum base-tip dimension: 58 mm. Minimum base-tip dimension: 36 mm. Maximum width dimension: 15 mm. Minimum width dimension: 14 mm.
*Color.*—Pinkish white (5 R 9/1) (10 R 9/1) in the basal areas and extending distally of the base and merging with margins which are strong reddish purple (10 P 5/10) in the proximal margin areas and moderate purplish red (7.5 RP 4/8) (5 RP 4/8) in distal marginal areas. Median distal blade color moderate red (2.5 R 5/8) (5 R 5/10).
Tube forming series of tepals:
*Number.*—8.
*Size (at full bloom).*—Perianth tube: Base to keel length — 33 mm. Interior major axis (at throat) — 9 mm. Interior minor axis (at throat) — 7 mm. Blades: Maximum length (keel to tip) — 36 mm. Minimum length (keel to tip) — 30 mm. Maximum width — 16 mm. Minimum width — 12 mm.
*Color.*—Perianth tube: Pale yellowish pink (10 R 9/2). Blades: Strong reddish purple (2.5 RP 4/10) and moderate purplish red (5 RP 5/10) in marginal blade areas. Pale purplish pink (5 RP 9/4) (7.5 RP 8/4) in basal and median blade areas. Carina (keel): Strong reddish purple (10 P 5/10) (2.5 RP 5/10).

Androecium:

*Stamen number.*— Tube attached group: 84. Basally united group: 20.

*Filaments.*—Color: Translucent white proximal area. Moderate purplish pink (10 P 7/6) (2.5 RP 7/6) in the distal area. Size (at full bloom): Length — Tube attached group: 47 mm. (avg.). Basally united group: 46 mm. (avg.). Diameter — About 0.3 mm. intermediate the opposite ends.

*Anthers.*—Color (before dehiscing): Pale yellow (5 Y 9/4).

Gynoecium (pistil):

*Style.*—Color: Moderate purplish pink (2.5 RP 7/6) (5 RP 7/6) in proximal portions. Moderate purplish red (5 RP 4/8) in distal portions. Size (at full bloom): Length — 63 mm. Diameter — About 0.8 mm. intermediate the opposite ends.

*Stigma.*—Color: Moderate reddish purple (2.5 RP 5/8) (2.5 RP 5/6). Size (lobe length): About 5.7 mm.

*Ovary.*—Color: Grayish greenish yellow (7.5 Y 7/4) (10 Y 7/4), moderate greenish yellow (7.5 Y 7/6). Size (at full bloom): Length (insertion to concavity base) — 11.5 mm. Major axis (distal end of concavity) — 8.5 mm. Minor axis (distal end of concavity) — 7.5 mm.

We claim:

1. The new and distinct variety of the Cactaceae family as described and illustrated and which is principally distinguished by a growth habit that combines the following characteristics:

a. A natural tendency to branch during the growth period preceding blooming without inducement by pruning.

b. A fast growth rate with resistances to nutrient deficiencies, fungus type diseases and flower bud abscission that are comparable to those of the 'Kris Kringle' and 'Lavender Doll' varieties.

c. Specimens with an upright compact appearance having phylloclades with generally shorter midribs than those of the 'Lavender Doll' variety and with generally thicker teeth than those of the 'Kris Kringle' variety, d. A flower which blooms from about 1 to 3 weeks later than that of the 'Kris Kringle' variety and has a bloom life of from about 6 to about 9 days and which has 1. A sepaloid series of free tepals with marginal blade areas in the inner and outer whorl members that in color are dominated by reddish purple, purplish red and/or purplish pink hues and with center fields in the inner whorl members that in color are dominated by pink and/or yellowish pink hues in the basal areas of the fields and by pink, red and/or reddish orange hues in the distal areas of the fields, 2. A perianth tube laminating series of tepals with center fields which extend into the apex areas of the tepal blades and in color are dominated by red, pink, purplish red and/or yellowish pink hues, and with lateral marginal areas which in color are dominated by reddish purple, purplish red and/or red hues, 3. A perianth tube forming series of basally united tepals that provide a perianth tube with a basic color which is dominated by yellowish pink and/or pink hues and on which is superimposed elongated, circumferentially spaced, stripes that are proximally extending colors found in the blade marginal areas and having blades with marginal areas which in color are dominated by reddish purple and/or purplish red hues that merge inwardly with a center blade field that in color is dominated by pink and/or purplish pin hues, and 4. A style which in color is dominated at its proximal end by a purplish pink hue and at its distal end by a purplish red hue.

* * * * *

UNITED STATES PATENT OFFICE

CERTIFICATE OF CORRECTION

Patent No. Plant 4,198 Dated January 24, 1978

Inventor(s) Barnell L. Cobia, et al

It is certified that error appears in the above-identified patent and that said Letters Patent are hereby corrected as shown below:

Delete Columns 1 thru 12 and substitute the attached Columns 1 thru 12 therefore.

Signed and Sealed this

*Sixteenth* Day of *January 1979*

[SEAL]

*Attest:*

RUTH C. MASON
*Attesting Officer*

DONALD W. BANNER
*Commissioner of Patents and Trademarks*

CACTACEAE PLANT

The invention relates to a new and distinct plant variety of the Cactaceae family and which has been named the *Zygocactus truncatus* 'Red Radiance' by the inventor.

Certain plant varieties of the Cactaceae family are well known in the foliage plant market and among those are those of the *truncatus* species of the Zygocactus genus. These varieties tend to bloom in the months of November and December in the Northern Hemisphere and hence they appear in the retail market area primarily during the Thanksgiving and Christmas seasons and wherein they are commonly referred to as a "Christmas Cactus".

The *Zygocactus truncatus* 'Kris Kringle' forms the subject matter of U.S. Plant Pat. No. 3,688 and has a heritage that includes the variety known commercially as 'Christmas Cheer' and the variety known as *Zygocactus truncatus* 'Parma'. It has a "reddish" colored bloom and a bloom life which provides a suitable shelf life at the retail level of sales. The variety also has a fast growth rate with substantial resistances to nutrient deficiencies and to fungus type diseases. The 'Kris Kringle' variety also has a substantial resistance to flower bud abscission and is endowed with a natural tendency to branch without inducement by pruning during the growth period preceding blooming. The growth rate, resistances, and branching tendencies are much sought after by growers of the so-called "Christmas Cactus" varieties.

The *Zygocactus truncatus* 'Lavender Doll' is yet another recent development among the so-called "Christmas Cactus" varieties and it forms the subject matter of a U.S. Plant Pat. No. 3,690. The 'Lavender Doll' variety has a heritage that also includes the 'Christmas Cheer' variety and it has a growth habit which includes the mentioned resistance characteristics attributed to the 'Kris Kringle' variety but the natural tendency to branch without inducement by pruning during the growth period preceding blooming is not as profuse as that resident in the 'Kris Kringle' variety. The 'Lavender Doll' has what may be called a "purplish" colored bloom and like the 'Kris Kringle' variety, has rapidly acquired a broad market acceptance that has created a demand among nurserymen for different colored varieties of the so-called "Christmas Cactus" types and which have the growth rate and natural resistances to nutrient deficiencies, fungus type diseases and flower bud abscission that are exhibited by the 'Kris Kringle' and 'Lavender Doll' varieties.

A general objective of the invention has been to develop a variety of the *truncatus* species which has the growth rate and previously mentioned resistance characteristics that are associated with the 'Kris Kringle' and 'Lavender Doll' varieties but which has color characteristics that are distinguishable from those of such varieties and a bloom that matures later than that of the 'Kris Kringle' variety.

The objectives of the invention have been fully realized by the development of the new plant variety described hereinafter in detail. The new plant variety was developed in a nursery located at Winter Garden, Fla., as a hybrid secured by cross-pollinating the flower of a plant specimen of a variety developed by the inventor from a vegetative mutation that appeared on a specimen of the 'Lavender Doll' variety with pollen from a plant specimen of the 'Kris Kringle' variety. The maternal variety is a research variety which has not appeared in the marketplace and it is distinguishable from the 'Lavender Doll' variety primarily by a growth habit which produces slightly larger phylloclades and specimens with somewhat poorer natural branching tendencies than those exhibited by the 'Lavender Doll' variety. The seeds taken from the fertilized seed pod of the maternal variety were cultivated at the mentioned nursery location, and after prolonged observation of the seedlings, the hybridized plant of the new plant variety was selected and asexually reproduced by the inventors at the Winter Garden nursery through a propagation of stem cuttings taken from the original hybrid plant.

Through successive propagations, it has been ascertained that specimens of the new plant variety generally resemble the parent varieties but are distinguishable from the parent varieties and from other related varieties known to the inventors by a growth habit which is evident in specimens propagated and grown under nursery conditions utilized in the growing of tropical plants at Winter Garden, Fla. as combining the following principal characteristics:

1. Specimens with an upright compact appearance having phylloclades with generally shorter midribs than those of the 'Lavender Doll' variety and with generally thicker teeth than those of the 'Kris Kringle' variety.

2. A natural tendency to branch without inducement by pruning during the growth period preceding blooming and which is comparable to that of the 'Kris Kringle' variety.

3. A fast growth rate with resistances to nutrient deficiencies, to fungus type diseases, and to flower bud abscission that are comparable to those of the 'Kris Kringle' and 'Lavender Doll' varieties.

4. A flower which blooms from about one to three weeks later than the 'Kris Kringle' variety and has a bloom life of from about 6 to about 9 days and which has a. a sepaloid series of free tepals with marginal blade areas in the inner and outer whorl members that in color are dominated by reddish purple, purplish red and/or purplish pink hues and with center fields in the inner whorl members that in color are dominated by pink and/or yellowish pink hues in the basal areas of the fields and by pink, red and/or reddish orange hues in the distal areas of the fields, b. a perianth tube laminating series of tepals with center fields which extend into the apex areas of the tepal blades and which in color are dominated by red, pink, purplish red and/or yellowish pink hues and with lateral marginal areas which in color are dominated by reddish purple, purplish red and/or red hues, c. a perianth tube forming series of basally united tepals that provide a perianth tube with a basic color which is dominated by yellowish pink and/or pink hues and on which is superimposed elongated, circumferentially spaced, stripes that are proximally extending colors found in the blade marginal areas and blades with marginal areas which in color are dominated by reddish purple and/or purplish red hues that merge inwardly with a center field that in color is dominated by pink and/or purplish pink hues, and d. a style which in color at its proximal end is dominated by a purplish pink hue and at its distal end is dominated by a purplish red hue.

The accompanying drawings serve, by color photographic means, to illustrate the new plant variety and wherein:

One sheet is a color photograph of an 11 month old plant specimen of the new plant variety with maturing buds, a second sheet contains photographs illustrating the bloom, and a third sheet embodies color photographs which further illustrate the bloom and parts thereof.

The following is a detailed description of the new plant variety with colors and hues, unless otherwise clearly indicated by the text through the absence of color notations, being named in accord with the ISCC-NBS method of designating colors (U.S. Department of Commerce, National Bureau of Standards, Circular 553, issued Nov. 1, 1955), the named colors being interpreted from color notations derived by comparison with the color specimens in the current "Neighboring Hues Edition" of the Munsell Book of Color, published by the Munsell Color Company, Inc., of Baltimore, Md. The following description is further based on observations of well fertilized plants of less than 1 year of age from initial propagation and which are grown under 50-75% shaded glasshouse nursery conditions in the Winter Garden, Fla., area and wherein temperatures range from 60° to 85° F. during the winter months, from 75° to 95° F. during the summer months and are ambient during intervening periods.

DETAILED PLANT DESCRIPTION

Name: *Zygocactus truncatus* 'Red Radiance'.

Parentage:

A. *Maternal.*—A research variety unavailable in the marketplace developed from a vegetative mutation that appeared on a plant specimen of the variety named *Zygocactus truncatus* 'Lavender Doll'.

B. *Paternal.*—*Zygocactus truncatus* 'Kris Kringle'.

Classification:

A. *Botanic.*—(Britton and Rose, *The Cactaceae,* Constable and Co., Ltd., London 1937, Vol. IV)—

| | |
|---|---|
| (1) Family: | Cactaceae |
| (2) Tribe: | Cereeae |
| (3) Sub-tribe: | Epiphyllanae |
| (4) Genus: | Zygocactus |
| (5) Species: | *truncatus* (Haworth) Schumann |

B. *Commercial.*—Thanksgiving-Christmas blooming cactus.

Form: Terrestrial, shade-loving, succulent, leafless plant with jointed and branched stems.

Stems:

A. *General.*—Irregular with usually mono-chotomous to polychotomous branching of both upright and pendulous, adventitiously rootable, flattened phylloclades that have a prominent midrib and prominently toothed lateral wings.

B. *Phylloclades.*—[1] General: Elongated and flat with transversely elongated, areole bearing, truncated apex, with inwardly tapering basal wing margins that merge through a broad usually pointed basal juncture with the phylloclade therebelow, and with an axillary areole associated with each tooth. [2] Midrib: (a) General — Extends longitudinally of phylloclade and continuously through joints with laterally tapering cortex at wing insertions. Pith surrounding vascular bundles that branch and provide lateral extensions of the vascular system to marginal teeth. (b) Texture — Smooth waxy epidermis with wax in small embedded scales and becoming corky in basal stem areas with age. (c) Size (2-6 mos.) — (1) Length: Usually between 36 and 55 mm. with the average for respective plant specimens being usually between 41 and 49 mm. (2) Thickness: Usually between 2.3 and 7.6 mm. with the average for respective plant specimens being usually between 3.5 and 4.5 mm. (d) Color (at maturity) — Commonly moderate yellow green (7.5 GY 5/6) (near 7.5 GY 5/4) (5 GY 5/6) (near 5 GY 5/4) and/or moderate olive green (7.5 GY 4/6) (7.5 GY 4/4). [3] Wings: (a) General shape—Generally flattened from midrib cortex to tooth insertions with slight thinning taper toward margins. (b) Margins — Toothed (modified leaves). (c) Texture — Succulent to leathery with smooth waxy epidermis having wax arranged in small embedded scales and becoming corky in basal plant areas with age. (d) Size (2-6 mos. old) — (1) Center thickness: Usually between 0.6 and 2.7 mm. (2) Width (as measured from phylloclade axis to most offset lateral areole): Usually between 7 and 19.5 mm. (e) Color (at maturity) — Commonly moderate yellow green (7.5 GY 5/6) (near 7.5 GY 5/4) (5 GY 5/6) (5 GY 5/4) and/or moderate olive green (near 7.5 GY 4/6). [4] Teeth: (a) General shape — Generally flattened and tapered along margins from wing insertions to an apex having a hyaline, single cell, pointed spine with nonpredictable bending. (1) Adaxial marginal shape: Generally straight to slightly convex. (2) Abaxial marginal shape: Generally straight with usually a slight median indentation which serves as a distal terminus for a straight to slightly convex proximal margin and as a proximal terminus for a straight to convex distal margin. (b) Orientation — Usually projects generally distally of phylloclade base in an alternate arrangement. (c) Margins — Entire. (d) Texture — Succulent to leathery with smooth waxy epidermis having wax in small embedded scales and becoming corky in basal plant areas with age. (e) Number — Usually from 6 to 8 per phylloclade. (f) Size (2-6 mos. old) — (1) Center thickness: Usually between 0.5 and 1.7 mm. (2) Areole to apex dimension (adaxial marginal side): Usually between 2 and 8 mm. for teeth located distally of basal teeth. (g) Color (at maturity) — Commonly moderate yellow green (7.5 GY 5/6) (7.5 GY 5/4) (5 GY 5/6) (5 GY 5/4) and/or moderate olive green (7.5 GY 4/6). [5] Areoles: (a) Terminal areole — Large elongated oval-shaped with several acicular bristles, copious multicellular hairs, and several buds that may mature into either new phylloclades or flowers. The opposite ends of the terminal areole are located adjacent to subsidiary areoles which are in turn located at the axils of teeth that are located at the distal end of phylloclade. (b) Axillary areoles — Acicular bristles without glochidia but having short, brownish to colorless, multicellular hairs. In areoles that are located below the teeth at the distal end of the phylloclade, there is usually only one bud that is frequently latent.

Buds: Unarmored, ovoid and chlorophyllous.

Flowers:

A. *General.*—Sessile, zygomorphic, usually solitary, terminal, perfect and epigynous with double hypanthium and tepals (undifferentiated whorled sepals and petals) having a spiral emergence as a perianth provided with a sepaloid series of free tepals, a tube laminating series of tepals, and a tube forming series of united tepals.

B. *Sepaloid series.*—[1] General: Free tepals inserted on top of ovary. [2] Shape: Deltoid in outer members of the whorl and grading inwardly in the whorl with tepals varying generally from lanceolate to elliptic. All tips are acute and margins are entire with sparse irregular teeth appearing mainly in apex areas of the inner members of the whorl. [3] Texture: Succulent and glabrous outer whorl members and grading inwardly in the whorl to silken blades with freshly basal areas. [4] Number: Usually from 8 to 10. [5] Size (at full bloom): (a) Base-tip dimension — Usually less than 35 mm. (b) Maximum width dimension — Usually less than 15 mm. [6] Color: (a) Outer Whorl members — Marginal blade areas that in color are dominated by reddish purple, purplish red and/or purplish pink hues and basal blade areas that in color constitute extension of the ovary color into the outer whorl member. Commonly grayish yellow (near 5 Y 7/4), pale greenish yellow (near 7.5 Y 8/4) (near 10 Y 8/4), grayish greenish yellow (near 7.5 Y 8/4) (7.5 Y 7/4) (near 10 Y 8/4) (10 Y 7/4), light greenish yellow (near 10 Y 8/6), moderate greenish yellow (7.5 Y 7/6) (near 10 Y 8/6) (10 Y 7/6), deep greenish yellow (near 10 Y 6/8), dark greenish yellow (near 10 Y 6/8) (10 Y 6/6), light yellow green (near 2.5 GY 8/6), moderate yellow green (2.5 GY 7/6) (2.5 GY 6/6) (near 2.5 GY 6/4) (2.5 GY 5/6) (near 5 GY 5/6) and/or strong yellow green (2.5 GY 7/8) (2.5 GY 6/8) in basal blade areas. Commonly strong reddish purple (2.5 RP 5/10) (2.5 RP 4/10), moderate purplish red (5 RP 5/10) (5 RP 5/8) (5 RP 4/8) (7.5 RP 5/10) (near 7.5 RP 5/8) (7.5 RP 4/8) (10 RP 5/10) (near 10 RP 5/8), deep purplish pink (7.5 RP 6/10) and/or dark purplish pink (near 7.5 RP 6/8) in the marginal blade areas. (b) Inner whorl members — Marginal blade areas that in color are dominated by reddish purple, purplish red and/or purplish pink hues which surround a center field that in color is dominated by pink and/or yellowish pink hues in the basal areas of the center field and by pink, red and/or reddish orange hues in the distal areas of the center field. Commonly strong reddish purple (2.5 RP 5/10) (2.5 RP 4/10), moderate purplish red (5 RP 5/10) (5 RP 5/8) (5 RP 4/8) (7.5 RP 5/10) (near 7.5 RP 5/8) (7.5 RP 4/8) (10 RP 5/10) (near 10 RP 5/8), deep purplish pink (7.5 RP 6/10) and/or dark purplish pink (near 7.5 RP 6/8) in the marginal blade areas. Commonly pinkish white (5 R 9/1) (10 R 9/1), pale pink (near 5 R 9/2), light pink (near 5 R 8/4), moderate pink (near 5 R 8/4), pale yellowish pink (10 R 9/2), light yellowish pink (near 7.5 R 8/4) (near 10 R 8/4) (near 2.5 YR 8/4) (near 5 YR 8/4) and/or moderate yellowish pink (near 7.5 R 8/4) (near 10 R 8/4) (near 2.5 YR 8/4) (near 5 YR 8/4) in the basal blade areas of the center field. Commonly deep pink (2.5 R 6/8) (near 5 R 6/10) (near 5 R 6/8), dark pink (5 R 6/6), grayish red (2.5 R 4/6), moderate red (near 2.5 R 5/10) (2.5 R 4/8) (5 R 5/10) (near 5 R 5/8) and/or moderate reddish orange (7.5 R 6/8) (7.5 R 5/10) (near 7.5 R 5/8) (10 R 6/8) (near 10 R 5/8) in the distal areas of the center field. [7] Orientation at full bloom: Usually acute to recurved.

C. *Tube laminating series.*—[1] General: Tepals inserted on ovary and basally united below the throat as outer laminations on the perianth tube and with progressively greater amounts of basal fusion inwardly in the whorl. [2] Shape: Grading inwardly in the whorl with outer members having blades which are narrowly elliptic, lanceolate, and/or oblanceolate and inner members which are elliptic to lanceolate. All tips are acute and all margins entire with sparse irregular teeth mainly in the apex areas. [3] Texture: Succulent, slightly fleshy basal areas with silken blades. [4] Number: Usually from 4 to 6. [5] Size (at full bloom): (a) Base-tip dimensions — Usually between 35 and 59 mm. (b) Maximum width dimensions — Usually between 11 and 16 mm. [6] Color: A center field in the blade which extends into the apex area of the tepal, which in color is dominated by purplish red, red, pink, yellowish pink and/or reddish orange hues which merges with lateral marginal blade areas that are located proximally of the apex area and in color are dominated by reddish purple, purplish red and/or red hues, and which merges with a basal area that in color is usually translucent white, pinkish white, pale pink and/or pale yellowish pink. Basal blade areas are usually translucent white, pinkish white (5 R 9/1) (10 R 9/1), pale pink (5 R 9/2) and/or pale yellowish pink (near 10 R 9/2). Commonly moderate purplish red (7.5 R 5/8) (10 RP 5/10) (10 RP 5/8), moderate red (2.5 R 5/8) (5 R 5/10) (5 R 5/8), deep pink (near 2.5 R 6/8) (5 R 6/10) (near 5 R 6/8), dark pink (near 5 R 6/6), dark yellowish pink (7.5 R 6/6) and/or moderate reddish orange (7.5 R 6/8) (7.5 R 5/10) (7.5 R 5/8) (near 10 R 6/8) in the center field. Commonly strong reddish purple (10 P 5/10) (10 P 4/10) (2.5 RP 4/10), moderate reddish purple (near 10 P 5/8) (2.5 RP 5/8), moderate purplish red (5 RP 5/10) (near 5 RP 5/8) (5 RP 4/10) (5 RP 4/8) (7.5 RP 4/8) (10 RP 4/10) (near 10 RP 4/8) and/or moderate red (2.5 R 4/10) (2.5 R 4/8) (5 R 4/10) in the lateral marginal areas. [7] Orientation at full bloom: Acute to recurved.

D. *Tube forming series.*—[1] General: Tepals basally united to form hollow perianth tube that is inserted on ovary and equipped with irregular carina (keel) at throat. [2] Shape: (a) Perianth tube — Elongated and terete. (b) Blades — Irregular and commonly lanceolate, oblanceolate and/or elliptic with acute tips and with tendencies for blade apex to be irregularly lacerate. (c) Carina (keel) — Transcending, thin and irregular. [3] Texture: (a) Perianth tube — Thick, succulent and slightly ribbed. (b) Blades — Translucent and silken. (c) Carina (keel) — Fleshy. [4] Blade number: Usually 8. [5] Size (at full bloom):

(a) Perianth tube — (1) Base to keel length: Usually between 31 and 38 mm. along axis of tube with average length difference between measurements along dorsal and ventral sides of respective specimens usually being between 0.5 and 6 mm. (2) Internal major axis (at throat): Usually between 7 and 11 mm. when measured perpendicular to axis of perianth tube. (3) Internal minor axis (at throat): Usually between 5 and 9 mm. when measured perpendicular to axis of perianth tube. (b) Blades — (1) Length (keel to tip): Usually between 23 and 37 mm. (2) Width (maximum): Usually between 10 and 17 mm. [6] Color (at full bloom): (a) Perianth tube — Basic color is dominated by yellowish pink and/or pink hues and provided with elongated circumferential spaced stripes or striations that are superimposed on the basic color and proximally extending colors found in blade marginal areas. Basic color is usually pale yellowish pink (near 5 YR 9/2) (10 R 9/2) and/or pale pink (near 5 R 9/2). (b) Blades — Marginal blade areas which in color are dominated by reddish purple and/or purplish red hues that merge inwardly with a center field that in color is dominated by purplish pink and/or pink hues. Commonly strong reddish purple (near 2.5 RP 5/10) (2.5 RP 4/10), moderate purplish red (5 RP 5/10) (near 5 RP 4/8) (7.5 RP 4/8) (10 RP 4/10) and/or dark purplish red (5 RP 3/8) in the marginal areas. Commonly pale purplish pink (5 RP 9/4) (near 5 RP 8/4) (7.5 RP 8/4) (near 7.5 RP 8/2), light pink (near 10 RP 8/4) (near 2.5 R 8/4) (near 5 R 8/4), moderate pink (near 10 RP 8/4) (near 2.5 R 8/4) (near 5 R 8/4), pale pink (5 R 9/2) and/or pinkish white (5 R 9/1) in the center field. (c) Carina (keel) — Dominated by reddish purple and/or purplish red hues. Commonly strong reddish purple (10 P 5/10) (2.5 RP 5/10) (10 P 4/10) (10 P 4/8), moderate reddish purple (2.5 RP 5/8) (2.5 RP 5/6) and/or moderate purplish red (5 RP 5/10) (near 5 RP 4/8) (7.5 RP 4/8) [7] Orientation at full bloom: Erect to recurved.

E. *Androecium (stamens).*—[1] General: Numerous exserted and diadelphous stamens with one group having filaments basally fused to the perianth tube and the other group having filaments basally united to form a nectary housing, thin annulus around the style and which is provided with a thin, deflexed, irregularly toothed margin or ruffle at the throat of the annulus. [2] Stamen number: (a) Tube attached group — Usually between 80 and 86. (b) Basally united group — Usually about 20. [3] Filament: (a) General — Translucent and glabrous with anther connective. (b) Shape — Long and terete. (c) Texture — Glabrous and silken. (d) Color — A translucent white proximal end area that merges distally with a proximal area which in color is dominated by a purplish pink hue. Commonly moderate purplish pink (10 P 7/8) (10 P 7/6) (2.5 RP 7/6) and/or pale purplish pink (near 10 P 8/4) (2.5 RP 8/4). (e) Size (at full bloom) — (1) Length: (a) Tube attached group — Usually between 34 and 51 mm. (b) Basally united group — Usually between 40 and 48 mm. (2) Diameter: Usually between 0.2 and 0.35 mm. intermediate the opposite ends. [4] Anthers: (a) General — Adnate with four longitudinally dehiscent pollen sacs. (b) Shape — Elongated. (c) Texture — Waxy. (d) Color (before dehiscing) — Usually pale yellow (5 Y 9/4) and/or pale yellowish green (7.5 Y 9/4).

F. *Gynoecium (pistil).*—[1] General: Compound, parietal placentation with united style surrounded by annular diffuse nectary at its insertion. [2] Style: (a) General — Stout and inserted in ovary. (b) Shape — Elongated and terete. (c) Texture — Fleshy and glabrous with short inner flutinous hairs at distal end. (d) Color — Basal area has color dominated by purplish pink hue that merges with a distal end color that is dominated by a purplish red hue. Commonly pale purplish pink (near 2.5 RP 8/4) and/or moderate purplish pink (2.5 RP 7/6) (5 RP 7/6) (7.5 RP 7/6) in basal area. Commonly moderate purplish red (5 RP 4/8) (7/5 RP 4/8) (10 RP 4/8) at distal end. (e) Size (at full bloom) — (1) Length: Usually between 57 and 65 mm. (2) Diameter: Usually between 0.7 and 0.9 mm. intermediate the opposite ends. [3] Stigma: (a) General — Exserted and erect with usually 7 or 8 inner marginally adhering lobes. (b) Shape — Elongated and tapering toward lobe tips and having relatively blunt apices. (c) Texture — Fleshy and smooth with short glutinous hairs. (d) Color — Commonly light reddish purple (10 P 6/8) (10 P 6/6), moderate reddish purple (near 10 P 5/8) (2.5 RP 5/8) (2.5 RP 5/6) and/or strong reddish purple (10 P 5/10) (2.5 RP 5/10) (2.5 RP 4/10). (e) Size (lobe length at full bloom) — Usually between 4.8 and 6.1 mm. [4] Ovary: (a) General — Epigynous with thin epidermis and distally located concavity and with single cavity having from 6 to 8 carpels with numerous ovules. (b) Shape — Terete and ribbed and generally broadening from insertion to floral end. (c) Texture — Succulent and glabrous with thin outer epidermis. (d) Color — Commonly grayish yellow (near 5 Y 7/4), pale greenish yellow (near 7.5 Y 8/4) (near 10 Y 8/4), grayish greenish yellow (near 7.5 Y 8/4) (7.5 Y 7/4) (near 10 Y 8/4) (10 Y 7/4), light greenish yellow (near 10 Y 8/6), moderate greenish yellow (7.5 Y 7/6) (near 10 Y 8/6) (near 10 Y 7/6), dark greenish yellow (near 10 Y 6/8) (10 Y 6/6), deep greenish yellow (near 10 Y 6/8), light yellow green (near 2.5 GY 8/6), moderate yellow green (2.5 GY 7/6) (2.5 GY 6/6) (near 2.5 GY 6/4) (2.5 GY 5/6) (near 5 GY 5/6) and/or strong yellow green (2.5 GY 7/8) (2.5 GY 6/8). (e) Size (at full bloom) — (1) Length (insertion to concavity base): Usually between 9 and 13 mm. (2) Major axis (distal end of concavity): Usually between 7 and 9 mm. (3) Minor axis (distal end of concavity): Usually between 6 and 8.5 mm.

Growing characteristics: A fast growth rate with an upright and compact (dense) appearance as evidenced by erect stems with heavy (frequent) branching and a bloom life (from initial tepal separation to initial tepal withering) of from about 6 to about 9 days. A natural tendency to branch without inducement by pruning during the growth period before blooming and a resistance to bud abscission and nutrient deficiencies and to fungus type diseases that are comparable to those of the 'Kris Kringle' and 'Lavender Doll' varieties.

The following is a general description of a specimen of the new plant variety that was grown from the propagation of a single phylloclade in a nursery at Winter Garden, Fla.

Age of plant: 6 months from initial propagation.
Branches from propagated cutting: 2.
Total number of phylloclades grown from cutting: 21.
General:

| Branch No. | No. of Phylloclades | Max. Length mm. | No. of Tips |
|---|---|---|---|
| 1 | 9 | 190 | 4 |
| 2 | 12 | 192 | 6 |

Midribs:

| Branch No. | Length (avg.) mm. | Thickness (avg.) mm. |
|---|---|---|
| 1 | 47 | 3.8 |
| 2 | 47 | 3.9 |

Wings:

| Branch No. | Center Thickness (avg.) mm. | Max. Width (Avg.) mm. |
|---|---|---|
| 1 | 1.5 | 11 |
| 2 | 1.3 | 13 |

Teeth:

| Branch No. | No./Phylloclades (avg.) | Center Thickness (avg.) mm. | Areole to Apex Dimension (avg.) mm. |
|---|---|---|---|
| 1 | 7 | 0.67 | 3.1 |
| 2 | 6 | 0.91 | 3.6 |

Phylloclade color: Moderate yellow green (7.5 GY 5/6) (5 GY 5/6) (near 5 GY 5/4).

The following is a general description of a flower of the new plant variety which was bloomed in December on a plant grown under shaded glasshouse nursery conditions in Winter Garden, Fla.

Bloom life: 8 days.
Sepaloid series of tepals:
(1) *Number.*—9.
(2) *Size (at full bloom).*—(a) Maximum base-tip dimension: 31 mm. (b) Minimum base-tip dimension: 3 mm. (c) Maximum width dimension: 12 mm.
(3) *Color.*—Grayish greenish yellow (7.5 Y 7/4) (10 Y 7/4) in major portion of the outer whorl members with margins which are moderate purplish red (5 RP 5/10) (7.5 RP 5/10). Inner whorl members strong reddish purple (2.5 RP 5/10) (2.5 RP 4/10) in the margin areas with median and basal colors which are light yellowish pink (near 7.5 R 8/4) (near 10 R 8/4) and/or moderate yellowish pink (near 10 R 8/4).
Tube laminating series:
(1) *Number.*—6.
(2) *Size (at full bloom).*—(a) Maximum base-tip dimension: 58 mm. (b) Minimum base-tip dimension: 36 mm. (c) Maximum width dimension: 15 mm. (d) Minimum width dimension: 14 mm.
(3) *Color.*—Pinkish white (5 R 9/1) (10 R 9/1) in the basal areas and extending distally of the base and merging with margins which are strong reddish purple (10 P 5/10) in the proximal margin areas and moderate purplish red (7.5 RP 4/8) (5 RP 4/8) in distal marginal areas. Median distal blade color moderate red (2.5 R 5/8) (5 R 5/10).

Tube forming series of tepals:
(1) *Number.*—8.
(2) *Size (at full bloom).*—(a) Perianth tube: (1) Base to keel length — 33 mm. (2) Interior major axis (at throat) — 9 mm. (3) Interior minor axis (at throat) — 7 mm. (b) Blades: (1) Maximum length (keel to tip) — 36 mm. (2) Minimum length (keel to tip) — 30 mm. (3) Maximum width — 16 mm. (4) Minimum width — 12 mm.
(3) *Color.*—(a) Perianth tube: Pale yellowish pink (10 R 9/2). (b) Blades: Strong reddish purple (2.5 RP 4/10) and moderate purplish red (5 RP 5/10) in marginal blade areas. Pale purplish pink (5 RP 9/4) (7.5 RP 8/4) in basal and median blade areas. (c) Carina (keel): Strong reddish purple (10 P 5/10) (2.5 RP 5/10).
Androecium:
(1) *Stamen number.*— (a) Tube attached group: 84. (b) Basally united group: 20.
(2) *Filaments.*—(a) Color: Translucent white proximal area. Moderate purplish pink (10 P 7/6) (2.5 RP 7/6) in the distal area. (b) Size (at full bloom): (1) Length — (a) Tube attached group: 47 mm. (avg.). (b) Basally united group: 46 mm. (avg.). (2) Diameter — About 0.3 mm. intermediate the opposite ends.
(3) *Anthers.*—(a) Color (before dehiscing): Pale yellow (5 Y 9/4).
Gynoecium (pistil):
(1) *Style.*—(a) Color: Moderate purplish pink (2.5 RP 7/6) (5 RP 7/6) in proximal portions. Moderate purplish red (5 RP 4/8) in distal portions. (b) Size (at full bloom): (1) Length — 63 mm. (2) Diameter — About 0.8 mm. intermediate the opposite ends.
(2) *Stigma.*—(a) Color: Moderate reddish purple (2.5 RP 5/8) (2.5 RP 5/6). (b) Size (lobe length): About 5.7 mm.
(3) *Ovary.*—(a) Color: Grayish greenish yellow (7.5 Y 7/4) (10 Y 7/4), moderate greenish yellow (7.5 Y 7/6). (b) Size (at full bloom): (1) Length (insertion to concavity base) — 11.5 mm. (2) Major axis (distal end of concavity) — 8.5 mm. (3) Minor axis (distal end of concavity) — 7.5 mm.

We claim:

1. The new and distinct variety of the Cactaceae family as described and illustrated and which is principally distinguished by a growth habit that combines the following characteristics:
(a) A natural tendency to branch during the growth period preceding blooming without inducement by pruning;
(b) a fast growth rate with resistances to nutrient deficiencies, fungus type diseases and flower bud abscission that are comparable to those of the 'Kris Kringle' and 'Lavender Doll' varieties;
(c) specimens with an upright compact appearance having phylloclades with generally shorter midribs than those of the 'Lavender Doll' variety and with generally thicker teeth than those of the 'Kris Kringle' variety;

(d) a flower which blooms from about one to three weeks later than that of the 'Kris Kringle' variety and has a bloom life of from about 6 to about 9 days and which has (1) a sepaloid series of free tepals with marginal blade areas in the inner and outer whorl members that in color are dominated by reddish purple, purplish red and/or purplish pink hues and with center fields in the inner whorl members that in color are dominated by pink and/or yellowish pink hues in the basal areas of the fields and by pink, red and/or reddish orange hues in the distal areas of the fields;

(2) a perianth tube laminating series of tepals with center fields which extend into the apex areas of the tepal blades and in color are dominated by red, pink, purplish red and/or yellowish pink hues, and with lateral marginal areas which in color are dominated by reddish purple, purplish red and/or red hues;

(3) a perianth tube forming series of basally united tepals that provide a perianth tube with a basic color which is dominated by yellowish pink and/or pink hues and on which is superimposed elongated, circumferentially spaced, stripes that are proximally extending colors found in the blade marginal areas and having blades with marginal areas which in color are dominated by reddish purple and/or purplish red hues that merge inwardly with a center blade field that in color is dominated by pink and/or purplish pink hues, and (4) a style which in color is dominated at its proximal end by a purplish pink hue and at its distal end by a purplish red hue.

* * * * *